(12) United States Patent
Bonnin

(10) Patent No.: US 7,434,935 B2
(45) Date of Patent: Oct. 14, 2008

(54) MEASUREMENT OF AN OPHTHALMIC LENS WEARER BEHAVIOR

(75) Inventor: Thierry Bonnin, Charenton le Pont (FR)

(73) Assignee: Essilor International (Compagnie Generale d'Optique), Charenton Cedex (FR)

(*) Notice: Subject to any disclaimer, the term of this patent is extended or adjusted under 35 U.S.C. 154(b) by 3 days.

(21) Appl. No.: 10/583,173

(22) PCT Filed: Dec. 14, 2004

(86) PCT No.: PCT/FR2004/003215

§ 371 (c)(1),
(2), (4) Date: Jun. 16, 2006

(87) PCT Pub. No.: WO2005/070284

PCT Pub. Date: Aug. 4, 2005

(65) Prior Publication Data

US 2007/0103641 A1    May 10, 2007

(30) Foreign Application Priority Data

Dec. 23, 2003   (FR) .................................. 03 15374

(51) Int. Cl.
*A61B 3/00* (2006.01)
*G02C 7/02* (2006.01)
(52) U.S. Cl. ...................... 351/246; 351/177
(58) Field of Classification Search ............... 351/219, 351/246, 247, 205, 228, 232, 163, 165, 177
See application file for complete search history.

(56) References Cited

U.S. PATENT DOCUMENTS

| 3,211,047 | A | 10/1965 | Heimberger |
| 4,338,002 | A * | 7/1982 | Gafert ........................ 351/246 |
| 5,489,953 | A | 2/1996 | Griffith |
| 6,827,443 | B2 | 12/2004 | Fisher et al. |
| 2002/0005932 | A1* | 1/2002 | Kerns et al. ................ 351/159 |
| 2002/0140899 | A1* | 10/2002 | Blum et al. ................. 351/159 |
| 2003/0107707 | A1 | 6/2003 | Fisher et al. |

FOREIGN PATENT DOCUMENTS

| FR | 1017134 | 12/1952 |
| FR | 1073615 | 9/1954 |
| GB | 121837 | 1/1919 |
| GB | 286932 | 3/1928 |

OTHER PUBLICATIONS

Fuller, James H., "Head movement prospensity", Experimental Brain Research 1992, pp. 152-164.
"User's manual revision F", OPM3609-002 C, Nov. 1993, Polhemus Incorporated, Colchester, Vermont.
Navarro et al., "Accommodation-dependent model of the human eye with aspherics", Opt. Soc. Am. A., vol. 2, No. 8/Aug. 1985.

* cited by examiner

*Primary Examiner*—Alicia M Harrington
(74) *Attorney, Agent, or Firm*—Fish & Richardson P.C.

(57) ABSTRACT

The present invention relates to the behavior of ophthalmic lens wearers. More specifically, it relates to systems and methods for measuring or characterizing ophthalmic lens wearer behavior.

9 Claims, 2 Drawing Sheets

MEASUREMENT OF AN OPHTHALMIC LENS WEARER BEHAVIOR

CROSS REFERENCE TO RELATED APPLICATIONS

This application is a US national stage under 35 U.S.C. §371 of PCT/FR2004/003215filed Dec. 14, 2004, which in turn claims priority to French application number 0315374filed Dec. 23, 2003. These applications are herein incorporated by reference.

TECHNICAL FIELD

The present invention relates to the behavior of ophthalmic lens wearers. More specifically, it relates to systems and methods for measuring or characterizing ophthalmic lens wearer behavior.

BACKGROUND

Ophthalmic lenses (or spectacle lenses) are supplied to the wearer in a mounting frame, so that the lenses are at a distance from the wearer's eyes. To look at a point in space, the wearer needs to move his or her head, perform an eye movement or combine a movement of the head and eyes. For example, in order to read a book of ordinary size, the wearer's head remains most frequently stationary and only the eyes move to follow the lines of text; as against this, when a spectacle wearer is driving a vehicle, he or she will generally employ a combination of head and eye movements.

For prescribing multifocal progressive lens spectacles, methods for customized prescription have been envisaged for many years now aimed at individually calculating or choosing the progressive lens design which is best adapted to the dynamic behavior of each spectacle wearer, notably in terms of head and eye movement.

An individual test makes it possible to assign to each individual wearer a coefficient that qualifies his propensity to rather move the head or rather move the eyes (head mover/eye mover). This behavioral coefficient presides over calculation of the best suited design. Thus, for example, for a wearer who tends to move the eyes rather than the head, a design having a fairly wide sharp vision field will be chosen. As against this, for a wearer who rather tends to move the head, and the eyes less, gentle progression at the periphery will be chosen to avoid an impression of swaying. Progression length can also be varied.

In practice, a critical step which is somewhat difficult to implement both from a technical as well as from a commercial point of view proves to be the individual test allowing the behavioral trend of each individual wearer to be determined. There has arisen the particular need for a device making it possible to perform in a simple, reliable and repetitive manner, measurements of head and eye movements of the spectacle wearer.

There do indeed exist already on the market devices for performing this measurement. Such devices mainly comprise:
- a fixed portion comprising several point light sources adapted to be activated alternately and distributed along a horizontal line, one central one facing the wearer and other side ones at each side of the central source at defined locations, and
- a mobile portion located on the wearer's head a bit like a hat and of which the angular position about the vertical is determined with respect to the fixed portion.

When a source at the side is lit up, the wearer will look at it by turning the head to a greater or lesser degree depending on his behavioral habits. one now measures the angle of rotation of the head and this is representative of the wearer's propensity to rather turn the head or the eyes when his view is drawn laterally.

One example of a device of this type and its implementation is discussed in the article "*Head movement propensity*" by James H Fuller, Experimental Brain Research 1992, pp 152-164. More recently, there has been a proposal to use, in a similar measurement method, modern wireless sensors of the type sold under the name 3SPACE® FASTRAK® by Polhémus Incorporated, Colchester, Vt., USA and described in the brochure "User's manual revision F", OPM3609-002 C, November 1993, or any more recent edition thereof.

These existing devices are satisfactory from a technical point of view but in practice are too expensive and complex or too impractical to operate for widespread use by opticians. There does exist a need for a simpler and less expensive measurement device.

More generally, for ophthalmic lens design, it can be useful to characterize the behavior of a wearer or given population. There is consequently a need for systems and methods allowing the behavior of an ophthalmic lens wearer to be characterized or measured.

SUMMARY

According to one aspect, this invention provides a method for measuring the behavior of the head and eyes of a spectacle wearer looking at a target, comprising the steps of:
   providing a target and equipping the spectacle wearer with a lens having at least two regions, a view of the target through one region of the lens being different from a view of the target through an adjacent region of the lens;
   when the spectacle wearer looks at the target, determining the region of the lens through which the spectacle wearer sees the target depending on how the spectacle wearer perceives the target, and
   calculating the spectacle wearer's head and eye movement as a function of the region determined.
   In one embodiment, the calculation step comprises:
   a step in which movement of the wearer's eyes with respect to the head is calculated as a function of the region determined, and
   a step in which movement of the wearer's head with respect to the trunk is measured as a function of the position of the target and of the movement of the wearer's eyes.

This determination step can be performed while masking one of the wearer's eyes.

According to a second aspect, there is provided a non-correcting ophthalmic lens having at least two regions, a view through one region of the lens differing from the view through an adjacent region of the lens.

The regions of the lens can extend vertically, or have parallel frontiers. It can also be arranged for a region to extend over an angular range of 8 to 10° under average wearing conditions.

Adjacent regions of the lens can have different colors and/or be separated by a black band. A central region of the lens is advantageously transparent.

There is also provided a set consisting of a non-correcting ophthalmic lens having at least two regions and of a target, a view of the target through one region of the lens differing from a view thereof through an adjacent region of the lens.

One region of the lens can filter light with a polarization different from the polarization of an adjacent region.

Further advantages and features of the invention will become more clear from the description which follows of embodiments thereof, given by way of example and with reference to the attached drawings.

DETAILED DESCRIPTION

The invention will be described below in an application to measurement of head and eye movement about vertical axes, in other words for a rotational movement of the head with respect to the trunk and from right to left and for a rotational movement of the eyes with respect to the head from left to right.

Figure 1:
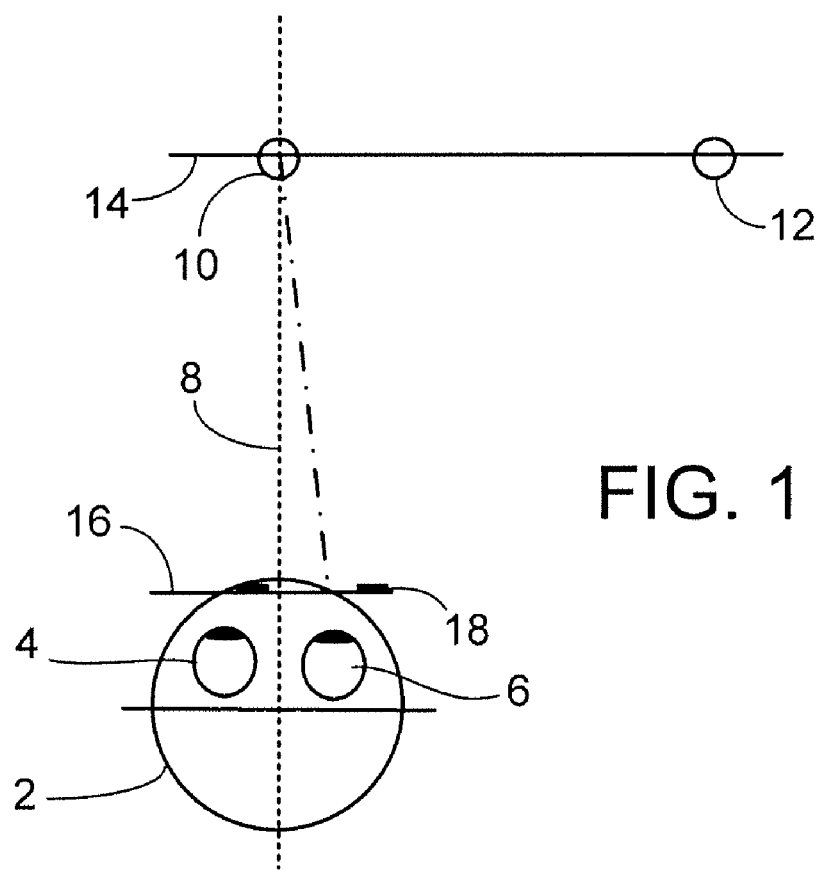
FIGS. 1-3 show a top sectional view of the head and eyes of a spectacle wearer, in various configurations.
Figure 2:
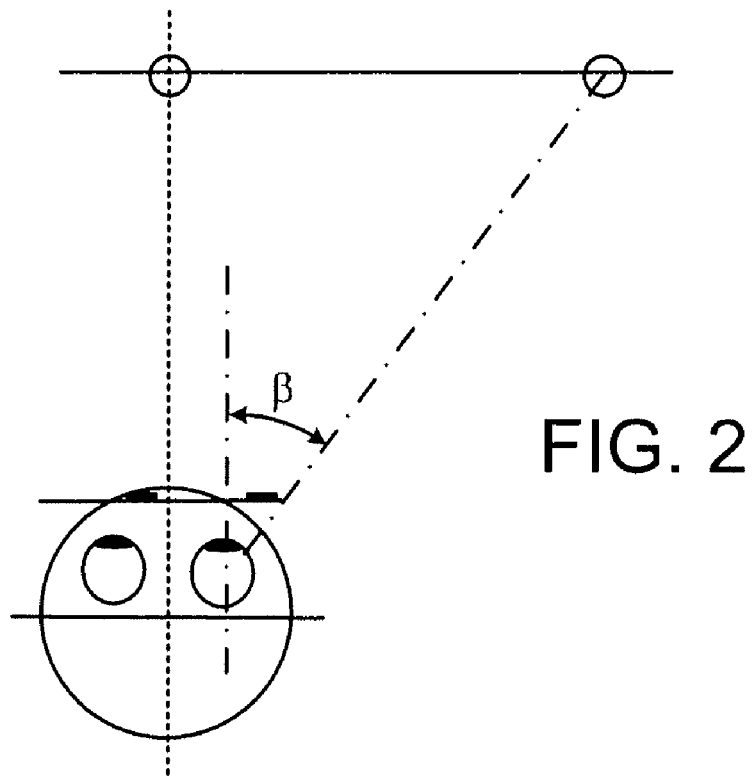
Figure 3:
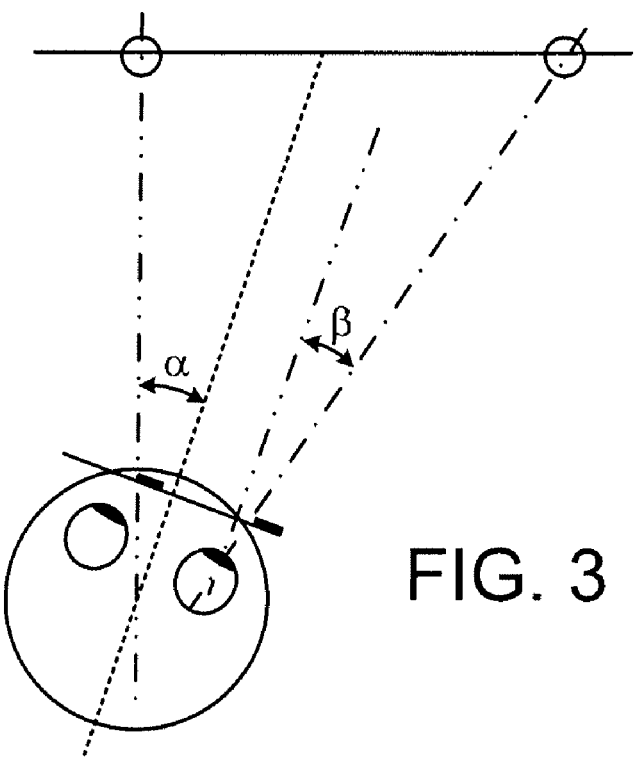

FIGS. 1-3 are top views in section of the head and eyes of a spectacle wearer in various configurations. In these drawings, the head 2 of the wearer which may turn with respect to the wearer's body about a vertical axis of rotation is shown; this axis is consequently perpendicular to the surface of the drawing sheet. The wearer's left eye 4 and right eye 6 are also shown diagrammatically. Each eye is able to turn with respect to the head about the eye's center of rotation which is not shown in the drawings. The dashed line 8 shows the main direction of vision in other words the vertical plane extending in front of the wearer's head; this is the median plane for both eyes 4, 6 of the wearer. Reference numeral 10 identifies a target or point in the object space located ahead of the wearer, at a given distance from the wearer; this distance is for example measured with respect to the axis of rotation of the head, indicated by a cross in the drawings. Reference numeral 12 identifies another target—another point in the object space; this point is located in a vertical plane 14, perpendicular to the main direction of vision and passing through the point 10; the angle between the points 10 and 12, seen from the wearer, is of the order of 40°. the dash-dot line in FIGS. 1 and 2 shows the direction of glance for the right eye. FIGS. 1 and 3 also show the lefthand 16 and righthand 18 lenses carried by the wearer.

FIG. 1 shows the spectacle wearer in a situation where he is looking straight ahead. The angle of rotation of the head with respect to the trunk is zero and the angle of rotation of the eyes with respect to the head is also zero. Thus, the main direction of glance corresponds to the plane extending from the wearer's trunk towards the point 10. The direction of glance is parallel to the main direction of vision.

FIGS. 2 and 3 show configurations in which the wearer is looking at the target or point 12. In the configuration of FIG. 2, the wearer is not turning his head with respect to his trunk but has simply turned his eyes with respect to his head; the angle α of rotation of the head with respect to the trunk remains zero, like in the configuration of FIG. 1. However, the angle of rotation β of the eyes with respect to the head is of the order of 40°. In the configuration of FIG. 3, the wearer has turned his head with respect to his trunk and is also turning his eyes with respect to his head. The wearer consequently looks at target 12 via a combination of head movement with respect to the trunk of an angle α of about 20° and an eye movement with respect to the head, through an angle β of the order of 20°.

FIGS. 1-3 consequently illustrate various wearer behaviors for looking at the target 12. The aim of this invention is to measure or characterize this behavior, in other words to determine how the wearer combines head movement and eye movement in order to look at a point in the object space which is not directly ahead of him.

Figure 4:
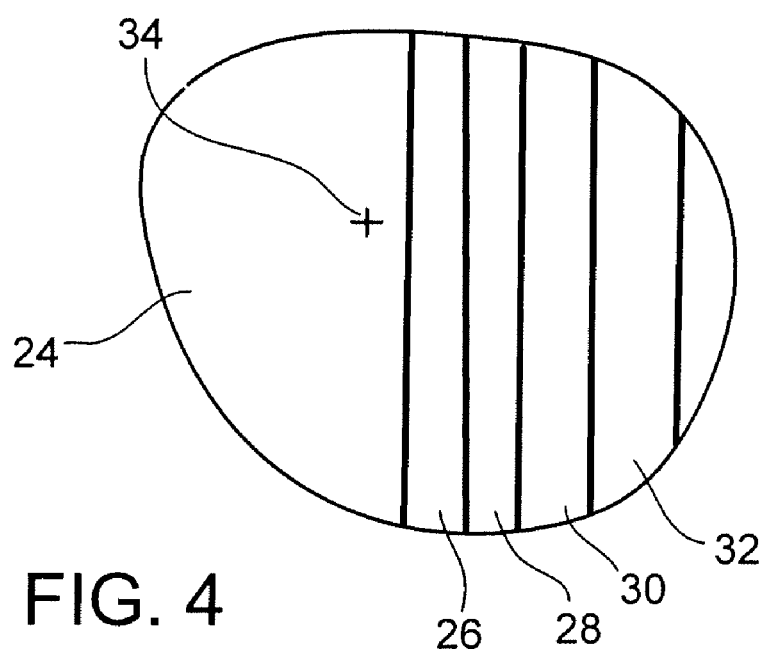
FIG. 4 is a front view of a lens according to the invention.

In one embodiment, the invention provides for the use, to measure wearer behavior, of a lens having differing regions of perception, as shown in FIG. 4. This figure shows diagrammatically lens 18 of FIG. 1, in a front view; in the example of FIG. 4, the head and eye movement behavior of the wearer about vertical axes are measured. As this figure shows, the lens is split up into various regions 24, 26, 28, 30 and 32 which are vertical—in other words substantially perpendicular to the direction of movement measured. These regions or fringes are five in number in the example, for reasons discussed below. The function of these fringes is to modify the wearer's perception of the target depending on the region through which he looks at the target. Various structural solutions are possible. In a first example, the fringes have differing colors, obtained for example using surface treatment of the lens or bulk treatment of the lens to impart thereto colors; surface treatment can comprise the application of a filtering film onto a lens surface, the application of a stained-glass window-type paint or, yet again, deposition by vacuum treatment. Bulk treatment can comprise coloring by dipping. One can, in order to apply these treatments, partially mask the lens. These various colors have the effect of the wearer perceiving differently the target depending on the region of the lens through which he looks at the target. One can for example employ the following colors for the various regions: red, green, transparent, blue, yellow. These different colors have the advantage of being easily perceived.

As an alternative to the colors, or in combination with these colors, engravings on the lens can also be used, for example hatchings which from one region to the other run in different directions. This solution has the advantage of being able to apply measurement to wearers suffering from color vision defects.

In another example, one can employ polarizing filters for the regions, having different directions of polarization; one then uses several close targets, having similar filters. The targets are chosen close so as to be able to be seen by the wearer through a same region of the lens; in the example of FIG. 4, the targets would be one above the other. Depending on the region through which the wearer looks at the targets, he will see one or the other of the targets. For example, for the various regions, one could employ polarized strips having a vertical polarization direction for the first and fourth strips and a horizontal polarization direction for the second and fifth strips. The third strip is, like in the previous example, a transparent strip. The target is constituted by two superimposed lamps of differing colors, one having vertical polarization and the other horizontal polarization; depending on the strip through which he looks at the target, the wearer will consequently see, running from the first to fifth strip: a lamp of a first color, a lamp of the other color, both lamps, the lamp of the first color, and then, finally, the lamp of the second color. The advantage over the previous solution is that the lens appears of uniform shade—like a sunglass lens, except for the central strip. This may be less disturbing for the spectacle wearer. One can also employ coloring (neutral in terms of polarization) for the central strip so as to provide the wearer with a uniformly shaded lens. In place of targets of different colors, one can employ targets of different shapes, thereby allowing the behavior of users having defective color perception to be measured. One can also combine differently shaped targets with varied polarizations.

One can also combine the various examples proposed in order to define regions on or in the lens; more generally, one can employ any solution known per se for modifying the perception or vision the wearer has of the target depending on the region of the lens through which he is looking at the target or targets.

One can use different colors or perceptions for each one of the regions; this solution has the advantage of the wearer not needing to count the regions he has run through; one can also only use two colors or two perceptions, alternating the colors or perceptions from one region to the next.

Measurement is done simply by equipping the wearer with a mounting frame having the lens in FIG. 4 and asking him or her to look at various targets. For this, a testing mounting frame can be used allowing the lens to be secured by clips; it is advantageous for half distance between the pupils to be adjustable to bring a central strip—the transparent strip in the previous example—opposite the wearer's eye. The half distance between the pupils is measured prior to mounting the lens using a pupil measuring instrument.

It is simpler to proceed with measurement one eye at a time; in effect, this avoids the need to look for corresponding positions on the color strips on the lefthand and right-hand lenses; although one can proceed successively with measurement on the right hand eye and then on the left eye, it turns out that wearer behavior is generally identical for both eyes. On FIGS. 1-3, measurement is being performed on the wearer's right eye. Consequently, as the drawings show, the left lens 16 is darkened and the wearer looks at the point 12 in the object space with the right eye. The figures consequently only show the direction of view starting from the right eye.

In the configuration of FIG. 1, the wearer is looking straight ahead. The head is at a central angular position and the direction of view originating from the right eye consequently passes through a region of the lens which is the first useful region starting from the nasal side of the lens. It is advantageous for the central region to be transparent, to allow ready realignment of vision.

In the configuration of FIG. 2, the wearer is looking at target 12; he is not turning his head (central head position), but simply his eyes. In this way, the angle α is zero and angle β between the direction of view originating from the right eye and the main direction of vision is of the order of 40°. The wearer looks at the target through a region of the lens which is the fifth useful region starting from the nasal side of the lens.

In the configuration of FIG. 3, the wearer is looking at target 12 by turning both his head and eyes. In this way, the angle α is some 20° and the angle β between the direction of view originating from the right eye and the main direction of vision is of the order of 20°. The wearer is looking at the target through a region of the lens which is the third useful region starting from the nose side of the lens.

Thus, depending on the wearer's behavior—FIGS. 1 and 2 only being two examples of possible behavior—the wearer has a different view of the target. It is consequently possible to simply ask the wearer to look at a target and to indicate the perception he has of the target in order to determine which region of the lens the wearer is looking at the target through. In the example of regions having different colors, the wearer in FIG. 2 could indicate one color while the wearer In FIG. 3 could indicate some other color.

One can determine the behavior of the wearer through a target which is located at the side to his right, as in the example of FIGS. 1-3; one can also employ a target located at the user's left side. In practice, it can be sufficient to provide three targets, one straight ahead of the wearer—to bring the wearer into the configuration of FIG. 1—and the two others at either side of the wearer, at angles of ±40°. It will be noted that, the position of the targets being fixed, the angle at which the wearer sees targets depends on the distance between the wearer and the plane containing the targets; it is advantageous for this distance to be measured as accurately as possible so that measurement will the accurate.

Determining the region of the lens through which the wearer is looking at the target makes it possible to calculate the angle of rotation of the eyes with respect to the head—or more precisely, a range of angular rotation of the eyes with respect to the head. This angular range depends on the position of the various regions on the lens and the position of the lens with respect to the eye; this position can be measured for the wearer, or can simply be modeled using the existing eye models and average or measured wearing conditions. Consider the eye model given in "*Accommodation-dependent model of the human eye with aspherics*", R. Navarro, J. Santamaria and J. Bescos, Vol. 2, No. 8/August 1985, Opt. Soc. Am. A. We can consider for wearer conditions, mean values equivalent to a distance of 27 mm between the center of rotation of the eye and the lens, a value of 12° pantascopic angle and a value of 3-5° for the contour.

In the example of FIG. 4, five regions had been provided on the lens, each region corresponds to an angular sector of around 8° for the angle of rotation β of the eyes with respect to the head. In order to have a substantially constant angular sector from one region to the next, the width of the regions on the lens increases from the point corresponding to the main direction of view towards the temple side or nasal side. In the example, we have shown a lens able to be used for the right eye, with color strip 26, 28, 30 and 32 of the temple side, which corresponds to a target on the right side of the wearer, like in FIG. 1 or FIG. 3. The remainder of the lens—on the left of strip 26 or to the right of strip 32, reference numeral 24—is transparent or is not colored. We have also shown in the drawing the point 34 which corresponds to the main direction of view. The lens can be mounted on a mounting frame allowing simple adjustment of height and separation.

In order to facilitate determination of the region of the lens, it is advantageous to provide black bands between the various regions of the lens. The bands make it possible to clearly mark the difference between the various regions and facilitate, for the wearer, the selection of the region through which he sees the target. A band can be 1 mm wide on the lens, corresponding to an angular range of the order of 2°. In order to allow the wearer to get his bearings, it is advantageous for the central or median region of the lens, corresponding to the wearer viewing to infinity, to be a transparent region. This allows the wearer to more readily get his or her bearings in the configuration shown in FIG. 1. Self-adhesive black bands can be employed.

Once the angle of rotation of the eyes with respect to the head has been determined, it is possible, depending on the position of the target, to determine head rotation. In fact, if the lateral position of the target is known, the angle of rotation of the head is determined as the angle that is necessary for the direction of gaze—taking account of the rotation of the eyes, to pass through the target. It will thus be understood that in the configuration of FIG. 2, the angle of rotation of the head is zero since the angle of rotation of the eyes,—measured by the lens region—substantially corresponds to the angle at which the user sees the target. As against this, in the configuration of FIG. 3, the angle of rotation of the eyes is of the order of 20°, while the target is, for the wearer, offset to the right by 40°; from this it can be deduced that the angle of rotation of the head is of the order of 20°. In practice, one can consider the two centers of rotation of head and eye to be common. This is justified by the distance between them which is so small compared to the distance from the target. This assumption gives good results and avoids having to measure the distance between the centers of rotation together with more complex calculation.

Comparative tests have shown, when the lens is according to the invention and the state-of-the-art system using the sensors from the Polhémus company, that wearing the lenses discussed above does not disturb wearer behavior.

Measurement is all the more accurate when the distance between the center of rotation of the eye and of the lens is known accurately and the distance between the wearer and the target or targets is known accurately. It is difficult to determine the distance between the center of rotation of the eye and the lens; one can nevertheless adapt the position of the lens so that the lens-eye distance is determined. Another solution consists in carrying out calibration of the measurement system by keeping the wearer's head stationary and moving the target and determining for what angular position of the target the wearer notices a change in color of the target.

In the example of FIG. 4, we have considered five regions; we can more particularly employ regions each covering an angular range of 8 to 10°. The central region would then cover eye vision in the range of ±4° to ±5° about the main direction of vision. One can then employ symmetrical regions at each side of the central region. The choice of four colors makes it possible to cover an angular range of −45° to ±45°, which is sufficient for the majority of spectacle wearers.

Obviously, this invention is not limited to the preferred examples given above. The regions of perception on the lens could run in another direction in order to measure wearer behavior about other axes of rotation than the vertical axes; for example, horizontal perception regions make it possible to measure the behavior of the wearer when he tilts his head upwardly and when he lowers or raises his eyes. If one were to employ regions of perception having a checkerboard pattern on the lens, this would allow combination of measurements in several directions. In the examples, the regions of perception are delimited by straight lines; one can also, depending on the behaviors to be measured, employ regions of perception that are delimited by curves. This could for example be the case for wearers who are accustomed to using progressive multifocal lenses.

The invention is not limited to the values for the number of regions and region width given in the examples of embodiments. One can, depending on requirements, perform measurements using fewer or more regions; nor is it essential for the different regions on the lens to be of identical size; one could for example, be interested in more accurate measurement over a given angular range.

The invention claimed is:

1. A method for measuring the behavior of the head and eyes of a spectacle wearer looking at a target, comprising the steps of:
   providing a target and equipping the spectacle wearer with a lens having at least two regions, a view of the target through one region of the lens being different from a view of the target through an adjacent region of the lens;
   when the spectacle wearer looks at the target, determining the region of the lens through which the spectacle wearer sees the target depending on how the spectacle wearer perceives the target, and
   calculating the spectacle wearer's head and eye movement as a function of the region determined.

2. The method of claim 1, wherein the calculation step comprises:
   a step in which movement of the wearer's eyes with respect to the head is calculated as a function of the region determined, and
   a step in which movement of the wearer's head with respect to the trunk is measured as a function of the position of the target and of the movement of the wearer's eyes.

3. The method of claim 1 or 2, wherein the determination step is performed while masking one of the wearer's eyes.

4. The method of claim 1, wherein the regions of the lens equipping the wearer extend vertically.

5. The method of claim 1, wherein the regions of the lens equipping the wearer have parallel frontiers.

6. The method of claim 1, wherein adjacent regions of the lens equipping the wearer have different colors.

7. The method of claim 1, wherein adjacent regions of the lens equipping the wearer are separated by a black band.

8. The method of claim 1, wherein a central region of the lens equipping the wearer is transparent.

9. The method of claim 1, wherein one region of the lens equipping the wearer filters light with a polarization different from the polarization of an adjacent region.

* * * * *